United States Patent [19]

Meilland

[11] Patent Number: Plant 7,623

[45] Date of Patent: Aug. 20, 1991

[54] ROSE PLANT—MEIXAPIC VARIETY

[75] Inventor: Alain A. Meilland, Antibes, France

[73] Assignee: The Conard-Pyle Company, West Grove, Pa.

[21] Appl. No.: 483,868

[22] Filed: Feb. 23, 1990

[51] Int. Cl.[5] ..... A01H 5/00

[52] U.S. Cl. ..... Plt./18

[58] Field of Search ..... Plt./17, 18, 19

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive fully double blossoms which are dawn pink on the upper surface and Venetian pink on the under surface. Such blossoms are very long lasting whether left on the plant or present in a vase. The plant exhibits an upright growth habit, semi-dull vigorous vegetation, and is well suited for growing as ornamentation in parks and gardens. Additionally, the plant is not particularly affected by cryptogamic diseases.

1 Drawing Sheet

SUMMARY OF THE INVENTION

The new variety of Hybrid Tea rose plant was discovered as a bud mutation of unknown causation of the Meikruza variety (U.S. Plant Pat. No. 5,864) which exhibits a distinctive blossom coloration. The blossoms of the new variety are of the same configuration as the parent variety and unlike the parent variety are dawn pink on the upper surface and Venetian pink on the under surface. The blossoms of the parent variety are light Indian yellow widely suffused with light salmon pink.

The new variety has been carefully studied and its distinctiveness with respect to blossom coloration has been confirmed. Had the new variety not been discovered and preserved it would have been lost to mankind.

It was found that the new variety of Hybrid Tea rose plant of the present invention possesses the following combination of characteristics:

(a) forms in abundance attractive very long lasting fully double blossoms which are dawn pink on the upper surface and Venetian pink on the under surface,
(b) exhibits an upright growth habit,
(c) exhibits vigorous vegetation,
(d) is particularly suited for growing in parks and gardens, and
(e) exhibits very good disease resistance.

The blossoms last a very long time whether cut or on the plant. Also, the blossom petals drop off cleanly.

The new variety well meets the needs of the horticultural industry for all uses and is particularly well suited for growing as attractive ornamentation in parks and gardens.

The new variety has been found to undergo asexual propagation by a number of routes, including budding, grafting, cuttings, etc. The characteristics of the new variety have been found to be strictly transmissible by such asexual propagation from one generation to another.

The new variety has been named the Meixapic variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indicia* understock and growing in greenhouses at Cap d'Antibes, France.

DETAILED DESCRIPTION

Figures 1, 2, 3, 4, 5, 6, 7, 8, 9, 10, 11, 12, 13, 14, 15, 16:
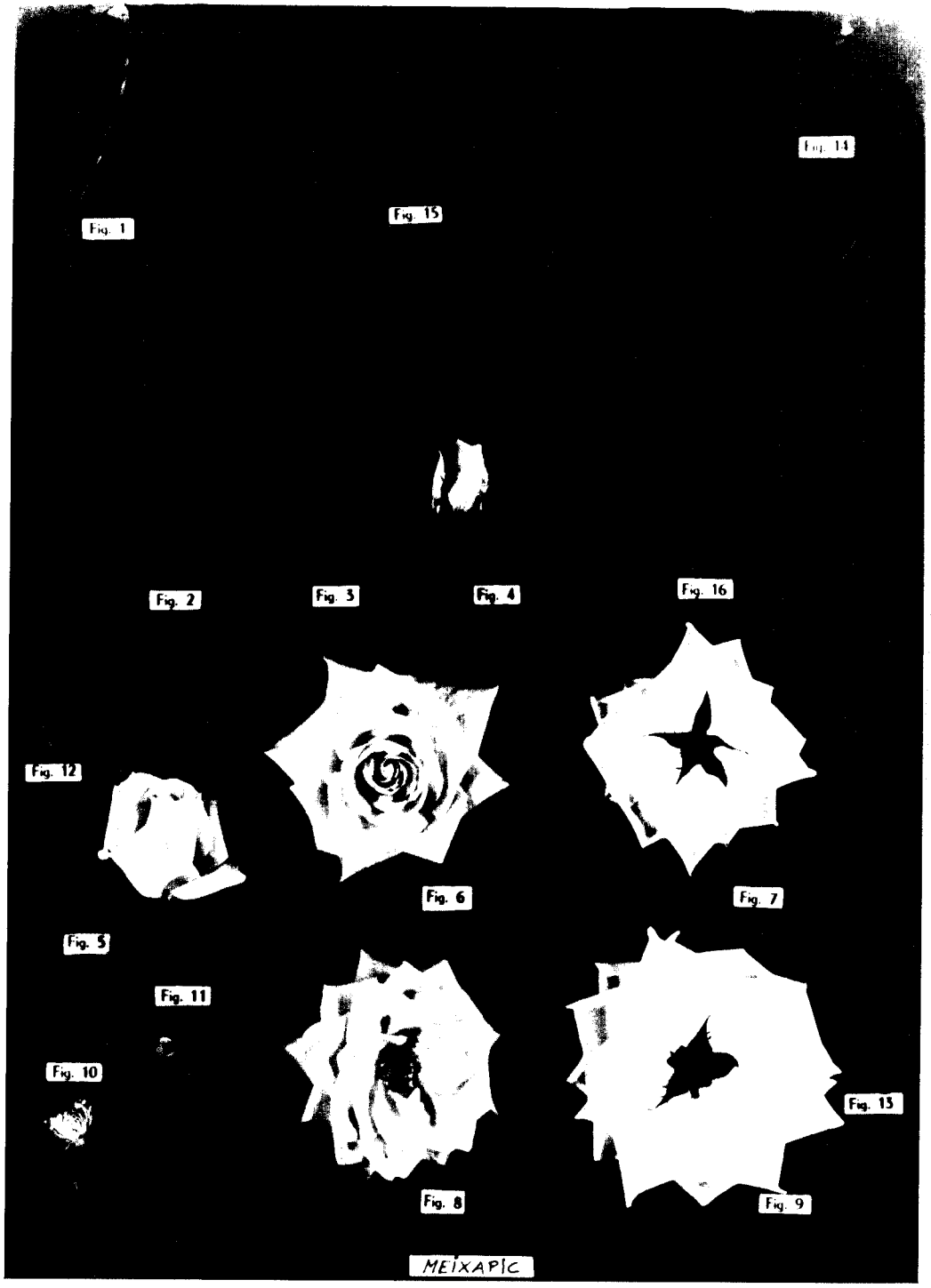
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower—plan view—obverse.
FIG. 7 illustrates a specimen of a fully open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of two leaves with three leaflets—plan view—upper surface on the top and under surface of the bottom.
FIG. 15 illustrates specimens of two leaves with five leaflets—plan view—under surface on the top and upper surface on the bottom.
FIG. 16 illustrates a specimen of a leaf with seven leaflets—plan view—upper surface.

The chart used in the identification of the colors is that of The Royal Horticultural Society (R.H.S. Colour Chart). The description is based on the observation of two year old plants made during November while budded on *Rosa indicia* understock and growing in greenhouses at Cap d'Antibes, France. The coloration in common terms precedes reference to the chart.

Class: Hybrid Tea.

Plant:

*Height.*—Plants which were pruned to a height of 85 cm. produce floral stems having a length of approximately 30 to 75 cm. When grown in fields at Wasco, Calif., the plant commonly is approximately 1.5 m. in height at the end of the growing season.

*Habit.*—Upright.

Branches:

*Color.*—Young stems: bronze green, Yellow-Green Group 146B, widely tinted with reddish brown. Adult wood: bronze green, Yellow-Green Group 146B.

*Thorns.*—Size: medium. Quantity: average. Color: pinkish on young stems and pinkish green changing to tan on mature wood.

Leaves:

*Stipules.*—Adnate, pectinate, fairly large and linear.

*Petioles.*—Upper surface: striped reddish brown on young foliage and medium green on adult foliage with more or less glandular edges. Under surface: bright green, more or less shaded with reddish brown, bear a few small prickles.

*Leaflets.*—Number: 3, 5 (rarely), and 7 (most often). Shape: elliptic generally wide and symmetrical, commonly have a rounded and asymmetrical base. Serration: single and regular. Texture: leathery. General appearance: foliage is somewhat dense, ample and semi-dull. Color (young foliage): Upper surface: reddish brown. Under surface: reddish brown. Color (adult foliage): Upper surface: dark green, Yellow-Green Group 147A. Under surface: medium green, Yellow-Green Group 147B, more or less stained with reddish brown.

Inflorescence:

*Number of flowers.*—Generally one per stem.

*Peduncle.*—Straight, rigid, and smooth. The length is approximately 8 cm. on average.

*Sepals.*—Upper surface: tomentose, greenish in coloration. Under surface: light green in coloration, smooth, the edges of the outer sepals are more or less appendiculated and glandular.

*Buds.*—Shape: conical when sepals open changing to cylindrical when petals open. Length: approximately 3.5 cm. on average when sepals open excluding the calyx. Size: medium. Color upon opening: Upper surface: empire rose, Red Group 48C. Under surface: light empire rose, Red Group 48D suffused with empire rose, Red Group 48C.

*Flower.*—Shape: initially cylindrical with substantially parallel sides, then changing to a cuplike configuration. Diameter: approximately 13.5 cm. on average. Color (when opening begins): Upper surface: dawn pink, Red Group 49A. Under surface: Venetian pink, Red Group 49C, suffused with empire Rose, Red Group 48D. Color (when blooming): Upper surface: dawn pink, Red Group 49A. Under surface: Venetian pink, Red Group 49C, suffused with empire rose, Red Group 48C. Color (at end of opening): Upper surface: Venetian pink, Red Group 49C, suffused with medium empire rose, Red Group 48C. Under surface: Venetian pink, Red Group 49C, suffused with medium empire rose, Red Group 48D. Fragrance: slight. Lasting quality: very long (e.g., approximately 10 to 14 days on average). Petal number: approximately 31 on average. Petal shape: rounded at the tip. Texture: very consistent. Petal drop: good. Stamen number: approximately 149 on average. Anthers: normal, light yellow edged with ochre. Filaments: very light yellow in coloration, of irregular heights. Pistils: approximately 96 on average. Stigmas: normal, strawlike in coloration. Styles: light yellow in coloration, tomentose at base, of irregular heights. Receptacle: light green, in longitudinal section it is in the shape of a pitcher.

Development:

*Vegetation.*—vigorous.

*Blooming.*—Abundant.

*Resistanct to diseases.*—Very good.

*Aptitude to forcing in a greenhouse.*—Very good.

I claim:

1. A new and distinct variety of Hybrid Tea rose plant characterized by the following combination of characteristics:

(a) forms in abundance attractive very long lasting fully double blossoms which are dawn pink on the upper surface and Venetian pink on the under surface,
(b) exhibits an upright growth habit,
(c) exhibits vigorous vegetation,
(d) is particularly suited for growing in parks and gardens, and
(e) exhibits very good disease resistance;

substantially as herein shown and described.

* * * * *

MEIXAPIC